United States Patent
Su et al.

(10) Patent No.: US 8,563,240 B2
(45) Date of Patent: Oct. 22, 2013

(54) NUCLEIC ACID SEQUENCING AND ELECTRONIC DETECTION

(75) Inventors: Xing Su, Cupertino, CA (US); Kai Wu, Mountain View, CA (US); David J. Liu, Fremont, CA (US)

(73) Assignee: Intel Corporation, Santa Clara, CA (US)

( * ) Notice: Subject to any disclaimer, the term of this patent is extended or adjusted under 35 U.S.C. 154(b) by 823 days.

(21) Appl. No.: 12/319,168

(22) Filed: Dec. 31, 2008

(65) Prior Publication Data
US 2010/0167938 A1 Jul. 1, 2010

(51) Int. Cl.
 C12Q 1/68 (2006.01)
 C12M 1/00 (2006.01)
 C12M 1/34 (2006.01)
 C12M 3/00 (2006.01)

(52) U.S. Cl.
 USPC .... 435/6.1; 435/283.1; 435/287.1; 435/287.2

(58) Field of Classification Search
 USPC ............ 435/6, 6.1, 283.1, 287.1, 287.2
 See application file for complete search history.

(56) References Cited

U.S. PATENT DOCUMENTS

| | | |
|---|---|---|
| 6,952,651 B2 | 10/2005 | Su |
| 6,972,173 B2 | 12/2005 | Su et al. |
| 7,005,264 B2 | 2/2006 | Su et al. |
| 7,238,477 B2 | 7/2007 | Su et al. |
| 7,476,501 B2 | 1/2009 | Chan et al. |
| 2003/0215816 A1 | 11/2003 | Sundararajan et al. |
| 2004/0110208 A1 | 6/2004 | Chan et al. |
| 2004/0259105 A1* | 12/2004 | Fan et al. ................ 435/6 |
| 2005/0019784 A1 | 1/2005 | Su et al. |
| 2005/0026163 A1 | 2/2005 | Sundararajan et al. |
| 2005/0186576 A1 | 8/2005 | Chan et al. |
| 2006/0029969 A1 | 2/2006 | Su et al. |
| 2006/0068440 A1 | 3/2006 | Chan et al. |
| 2006/0141485 A1 | 6/2006 | Su et al. |
| 2006/0199193 A1 | 9/2006 | Koo |
| 2007/0059733 A1 | 3/2007 | Sundararajan et al. |
| 2007/0231790 A1 | 10/2007 | Su |
| 2007/0231795 A1 | 10/2007 | Su |
| 2008/0032297 A1 | 2/2008 | Su et al. |
| 2008/0160630 A1 | 7/2008 | Liu et al. |

OTHER PUBLICATIONS

Fritz, Jurgen et al.,"Electronic detection of DNA by its intrinsic molecular charge", Proc. Natl. Acad. Sci. USA, Oct. 29, 2002, vol. 99, No. 22, pp. 14142-14146.
Chen, Robert J. et al., "Noncovalent functionalization of carbon nanotubes for highly specific electronic biosensors", Proc. Natl. Acad. Sci. USA, dated Apr. 29, 2003, vol. 100 No. 9, pp. 4984-4989.

(Continued)

*Primary Examiner* — Robert T. Crow
(74) *Attorney, Agent, or Firm* — Pillsbury Winthrop Shaw Pittman LLP

(57) ABSTRACT

Embodiments of the present invention provide devices methods for sequencing DNA using arrays of reaction regions containing sensors to monitor changes in solutions or bound molecules contained in the reaction regions. Additional embodiments provide devices and methods for sequencing DNA using arrays of reaction regions that allow for optical monitoring of solutions in the reaction regions. Chemical amplification schemes that allow DNA to be sequenced in which multiple nucleotide addition reactions are performed to detect the incorporation of a base are disclosed. By sequencing DNA using parallel reactions contained in large arrays, DNA can be rapidly sequenced.

16 Claims, 13 Drawing Sheets

(56) References Cited

OTHER PUBLICATIONS

Gao, Guangxia, et al., "Conferring RNA polymerase Activity to a DNA polymerase: A single residue in reverse transcriptase controls substrate selection," Proc. Natl. Acad. Sci. USA, Biochemistry, vol. 94, pp. 407-411, Jan. 1997.

Delucia, Angela M. et al., "An error-prone family Y DNA polymerase (Din B homolog from *Sulfolobus solfataricus*) uses a 'stericgate' residue for discrimination against ribonucleotides," Nucleic Acids Research, vol. 31. No. 14, (2003) pp. 4129-4137.

Star, Alexander et al., "Electronic Detection of Specific Protein Binding Using Nanotube FET Devices," Nano Letters, vol. 3, No. 4., Mar. 5, 2003, p. 459-463.

Kling, Jim, "Ultrafast DNA sequencing," Nature Biotechnology, Dec. 2003, v. 21, No. 12, pp. 1425-1427.

U.S. Appl. No. 11/073,160 "Sensor Arrays and Nucleic Acid Sequencing Applications" filed Mar. 4, 2005.

Elibol, Oguz H. et al., "Localized heating and thermal characterization of high electrical resistivity silicon-on-insulator sensors using nematic liquid crystals" Applied Physics Letters, 93, 131908, Sep. 30, 2008.

Elibol, Oguz H. et al., "Nanoscale Thickness Double-gated Field Effect Silicon Sensors for Sensitive pH Detection in Fluid," Applied Physics Letters, 92(2008) 193904.

Rolka, David et al.,"Integration of a Capacitive EIS Sensor into a FIA System for pH and Penicillin Determination," Sensors, (2004) pp. 84-94.

Janicki, Marcin et al.,"Ion Sensitive Field Effect Transistor Modelling for Multidomain Simulation Purposes," Microelectronics Journal, 35 (2004) pp. 831-840.

U.S. Appl. No. 11/753,361, "Methods to Increase Nucleotide Signals by Raman Scattering," filed May 24, 2007.

Ronaghi, Mostafa et al., "DNA Sequencing: A Sequencing Method Based on Real-Time Pyrophosphate," Science, vol. 281, No. 5375 (1998) pp. 363-365.

* cited by examiner

NUCLEIC ACID SEQUENCING AND ELECTRONIC DETECTION

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, and U.S. patent application Ser. No. 11/969,600, entitled "Electronic Sensing for Nucleic Acid Sequencing," filed Dec. 31, 2007, now pending, the disclosures of which are incorporated herein by reference.

BACKGROUND OF THE INVENTION

1. Field of the Invention

The embodiments of the present invention relate generally to methods and devices for nucleic acid sequencing and the electronic detection of nucleic acid sequencing reactions.

2. Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, coronary heart disease, diabetes, and sickle cell anemia. Determination of the entire three billion nucleotide sequence of the human genome has provided a foundation for identifying the genetic basis of such diseases. A determination of the sequence of the human genome required weeks or months to accomplish. The need for nucleic acid sequence information also exists in personalized medicine, research, environmental protection, food safety, biodefense, and clinical applications, such as for example, pathogen detection (the detection of the presence or absence of pathogens or their genetic variants).

Thus, because DNA sequencing is an important technology for applications in bioscience, such as, for example, the analysis of genetic information content for an organism, tools that allow for faster and or more reliable sequence determination provide significant value. Applications such as, for example, population-based biodiversity projects, disease detection and diagnosis, prediction of effectiveness of drugs (personalized medicine), biomarker discovery through disease-genotype association, genotyping using single-nucleotide polymorphisms, and drug development through gene expression profiling studies stimulate the need for simple and robust methods for sequencing long or short lengths of nucleic acids (such as, for example, those containing 1-20 bases). Sequencing methods that provide increased accuracy and or robustness, decreased need for sample preparation, and or high throughput are valuable analytical and biomedical tools.

DETAILED DESCRIPTION OF THE INVENTION

Figure 1:
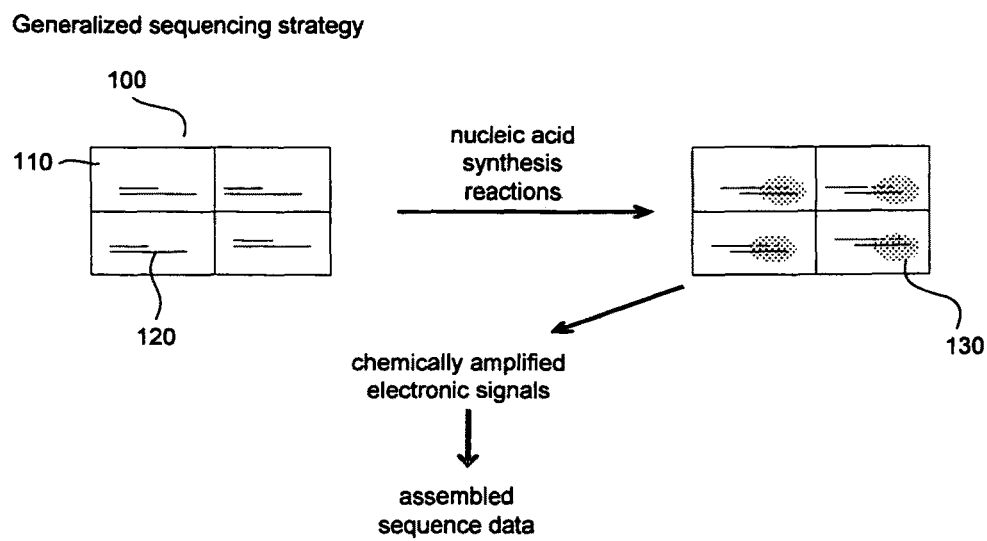
FIG. 1 provides a simplified diagram of a method for sequencing nucleic acids employing a sensor array to detect reaction products.

Embodiments of the present invention provide devices and methods for sequencing nucleic acids and nucleic acid detection. In general, nucleic acids (polynucleotides) that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, a synthetic polydeoxyribonucleic acid sequence, or RNA (ribonucleic acid). A polynucleotide, including an oligonucleotide (for example, a probe or a primer) can contain nucleoside or nucleotide analogs, or a backbone bond other than a phosphodiester bond. In general, the nucleotides in a polynucleotide are naturally occurring deoxyribonucleotides (or deoxyribonucleosides), such as adenine, cytosine, guanine or thymine linked to 2'-deoxyribose, or ribonucleotides (or ribonucleosides) such as adenine, cytosine, guanine or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides (nucleosides) to produce synthetic polynucleotides. The incorporation of non-naturally occurring nucleotide analogs or bonds linking the nucleotides or analogs can be particularly useful where the polynucleotide is to be exposed to an environment that can contain nucleolytic activity (including endonuclease and exonuclease activity), since the modified polynucleotides can be less susceptible to degradation.

Virtually any naturally occurring nucleic acid may be sequenced including, for example, chromosomal, mitochondrial, or chloroplast DNA or ribosomal, transfer, heterogeneous nuclear, or messenger RNA. Additionally, methylated DNA and small interfering RNA (siRNA) and microRNA (miRNA) can be sequenced. RNA can be converted into more stable cDNA through the use of a reverse transcription enzyme (reverse transcriptase). Additionally, non-naturally occurring nucleic acids that are susceptible to enzymatic synthesis and degradation may be used in embodiments of the present invention.

Methods for preparing and isolating various forms of nucleic acids are known. See for example, Berger and Kimmel, eds., *Guide to Molecular Cloning Techniques*, Academic Press, New York, N.Y. (1987); and Sambrook, Fritsch and Maniatis, eds., *Molecular Cloning: A Laboratory Manual 2nd Ed.*, Cold Spring Harbor Press, Cold Spring Harbor, N.Y. (1989). However, embodiments of the present invention are not limited to a particular method for the preparation of nucleic acids.

Methods are provided for sequencing nucleic acids in which amplification of the nucleic acid sample (i.e., increasing the number of copies of nucleic acid molecules in the sample) optionally does not have to occur. As much as one third of the error reported during the sequencing of a nucleic acid sample has been reported to be due to errors introduced during amplification of the nucleic acid sample. By not amplifying the sample to be sequenced, amplification-related errors can be avoided. Additionally, avoiding amplifying a sample avoids the concentration bias that can develop when a sample is amplified. The concentration bias that occurs during amplification is a result of the selective amplification advantage found for certain sequence populations, such that some sequences are amplified preferentially to a greater extent than other sequences. Because amplification-related errors are reduced, the methods of the present invention are useful for surveying for rare mutations among samples having a variety of components (mixed background components).

Referring now to FIG. 1, a depiction of a generalized sequencing strategy according to embodiments of the invention is provided. In FIG. 1, an array of electronic sensors 100, such as, for example, field-effect-transistors (FETs), having reaction regions 110 and immobilized DNA molecules 120 is shown. Sensors 100 can also be nano or micro-electrodes where the signal is measured by impedance meter(s), for example. One DNA molecule to be sequenced is immobilized per sensor region 110 in this example. Before sequencing a sample of DNA, overlapped DNA fragments are immobilized randomly on the array so that statistically one DNA molecule 120 occupies the reaction region 110 of a sensor. A sample of DNA can be fragmented into smaller polymeric molecules using, for example, restriction enzymes or mechanical forces (shearing). Nucliec acid synthesis reactions are performed and amplified chemical products of the synthesis reactions 130 are created in the sensor regions (wells) 110. The identified base position is then filled with a nuclease resistant base, and the reaction is repeated to determine a matching base for the next available position on the DNA strand to be sequenced. In this example, the amplified chemical products 130 are detected electronically and sequence data for the immobilized DNA molecules is assembled. Amplified chemical products 130 in a reaction region 110, such as, for example, a gate of a FET, change the composition of chemical species, ionic conditions, or pH of the region and thus alter the current flow between the source and the drain or capacitance between electrodes. Reaction conditions and their corresponding positions and electronic signals are recorded and analyzed with a computer and software. Data from sensors having no immobilized nucleic acid sample or a plurality of immobilized samples can be electronically distinguished.

Figure 2:
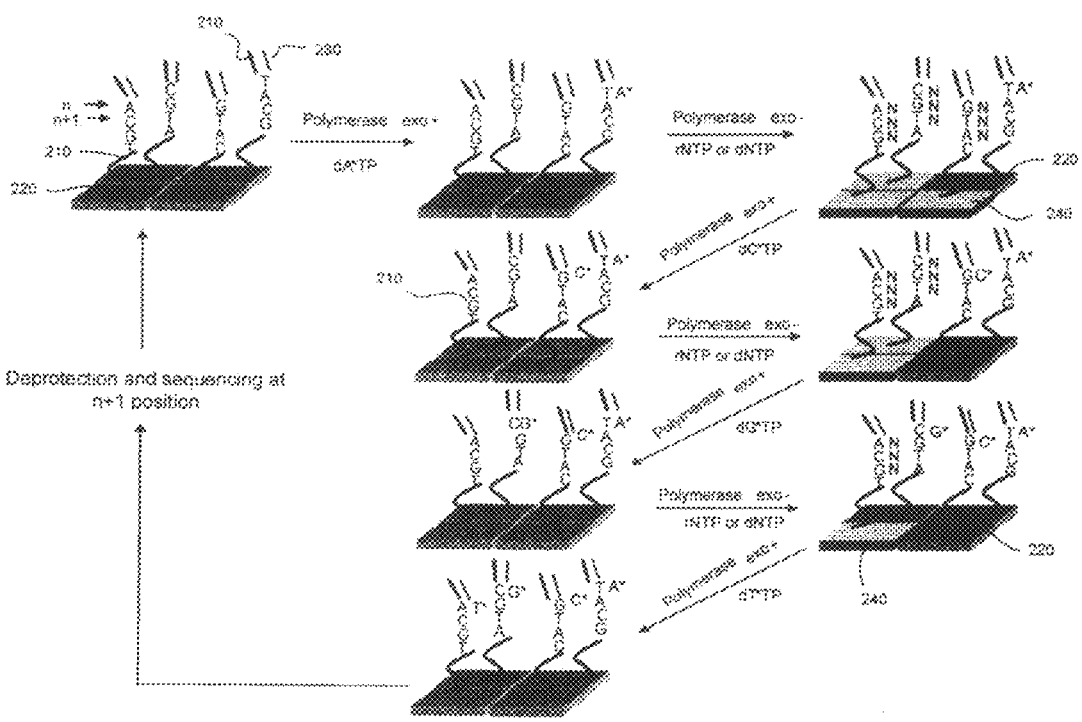
FIG. 2 shows a general scheme for sequencing nucleic acids using an array of sensors and sequential reversible determination.

FIG. 2 provides an exemplary method for sequencing nucleic acids using an array of sensors and the chemical amplification of sequencing signals generated through sequential reversible termination and DNA synthesis reactions. In FIG. 2, nucleic acids to be sequenced 210 are immobilized on sensors 220, such that statistically there is one DNA molecule 210 immobilized on one sensor 220, and the DNA molecules to be sequenced 210 are primed with a complementary sequence of DNA 230 (a primer) that is terminated with an exonuclease resistant nucleotide. Alternatively, a primer can be immobilized, and the DNA to be sequenced hybridized to the primer. A solution comprising a polymerase enzyme (polymerase exo+ which is a polymerase enzyme that is non-discriminatory toward nucleotides having modified phosphate groups and reversibly blocked 3' ends and which possesses exonuclease activity, such as for example, T4 and T7 DNA polymerases and Therminator II DNA polymerase which is able to incorporate modified nucleotide analogs) and a nuclease resistant blocking nucleotide (such as, for example, dA*TP, dG*TP, dU*TP, dT*TP, or dC*TP, the "*" indicating that the regular dATP, dGTP, dUTP, dTTP, or dCTP is modified to possess two functionalities: (a) a nuclease resistance and (b) 3' reversible polymer synthesis termination (blocked)) is supplied to the surface of the array of sensors 220 and the DNA primer 230 is then extended by a nucleotide that is complementary to the "$n^{th}$" base presented by the DNA to be sequenced 210. If the nuclease resistant blocking nucleotide provided is not complementary to the "$n^{th}$" base presented by the DNA to be sequenced 210, then no nucleotide is added to the primer, in other words, no DNA synthesis reaction occurs. The blocking nature of the nucleotide prevents further chain elongation for the primer sequence (synthesis termination) to which it is attached. The primers 230, for which the DNA molecules to be sequenced 210 that were not complementary in the "$n^{th}$" position to the supplied nuclease resistant blocking nucleotide, remain unblocked and available for further DNA elongation reactions. A solution comprising a polymerase enzyme ("polymerase exo–"which is a polymerase enzyme that does not have exonuclease activity, such as for example, Klenow fragment polymerase, Taq DNA polymerase, or Therminator II DNA polymerase) and nucleotides (such as, for example, dATP, dGTP, dTTP, and dCTP; ATP, GTP, UTP, and CTP; nucleotide analogs thereof; or labeled nucleotides thereof) are supplied to the surface of the array of sensors 220 and the DNA primer 230 is then extended and or optionally deconstructed for primers 230 that are not terminated with a blocking nucleotide. The extension of the DNA primer 230 by, for example, 10 to 1000 nucleotides creates signal that is detected by the sensors 240. The signal that is created is an amplified signal: in the sense that the addition of a nucleotide to the DNA primer 230 a plurality of times creates bound charges due to nucleotide incorporation and released reaction products (e.g., PPi and protons) that can be detected by an electronic sensor, in the form of, for example, a change in pH, a change in ionic concentration, a change in chemical species (generation of PPi), or a change in surface charge distribution (bound negative charges from the synthesized DNA polymer. Performing the DNA synthesis reaction a plurality of times increases the concentration of the reaction products each time a nucleotide is added to the primer DNA molecule 230 and increases the amount of signal for detection. For example, adding five nucleotides to the primer strand provides a signal that is amplified five times over the signal that is created when only one nucleotide is added to the primer DNA molecule 230. A signal (a change in reactants) is detected by sensors 240 but not by sensor(s) 220 where a complementary blocking nucleotide was added in the previous reaction. In this example, the signals detected can be considered negative signals since observing a signal in a sensor indicates that no complementary nucleotide was added in the previous reaction and that the next complementary nucleotide for the immobilized DNA to be sequenced 210 is not adenosine. The sensor providing no signal indicates that a blocking complementary nucleotide was added to the primer DNA molecule 230. Infrequently, a lack of signal could also indicate an error such as no DNA is immobilized on the sensor 220 or that the DNA has been compromised or otherwise degraded. This type of error can be subtracted for since a sensor having no DNA immobilized or a compromised sample that is unable to grow (polymerize) will give no signal in further reactions. Similarly, a sensor having more than one different molecule of DNA will provide data through a series of sequencing reactions indicating that more than one type of nucleotide has been added during a particular reaction cycle. The data from the sensor having more than one different DNA can be discarded. For sequences having repetitive bases, the incorporation of a nuclease resistant blocking nucleotide can prevent the addition of another nucleotide until the 3' reversible blocking group is cleaved. Redundant reactions can optionally be used to increase accuracy. After signal detection and removal of the reactants, a new set of reactants (polymerase exo+ and another one of the four nuclease resistant blocking nucleotides) is added. The nuclease activity of the polymerase enzyme removes the regular nucleotides that were added in order to detect a signal. Optionally, additional nuclease can also be used. Exemplary nuclease enzymes include, exonuclease T, Bal-31 nuclease, and RNase H, which are all commercially available. After completing a reaction cycle for the $n^{th}$ position in which each of the four nuclease resistant blocking nucleotides is used in separate reactions and signals are detected, the DNA synthesis blocking group is then removed and the sequencing process can proceed for the "$n+1^{th}$" position. A solution comprising a polymerase enzyme (polymerase exo+) and a nuclease resistant blocking nucleotide (such as, for example, dA*TP, dG*TP, dU*TP, dT*TP, or dC*TP) is once again supplied to the surface of the array of sensors 220 and the DNA primer 230 is then extended by a nucleotide that is complementary to the "$n+1^{th}$" base presented by the DNA to be sequenced 210. The primers 230, for which the DNA molecules to be sequenced 210 that were not complementary in the "$n+1^{th}$" position to the supplied nuclease resistant blocking nucleotide, remain unblocked and available for further DNA elongation reactions. A solution comprising a polymerase enzyme ("polymerase exo–") and nucleotides (such as, for example, dATP, dGTP, dTTP, and dCTP; ATP, GTP, UTP, and CTP; nucleotide analogs thereof; or labeled nucleotides thereof) is supplied to the surface of the array of sensors 220 and the DNA primer 230 is then extended for primers 230 that are not terminated with a blocking nucleotide. The extension of the DNA primer 230 once again creates signal that is detected by the sensors 240. These reactions are repeated a plurality of times to assemble the sequences of the DNA 210 immobilized in the sensors 220.

Figure 3:
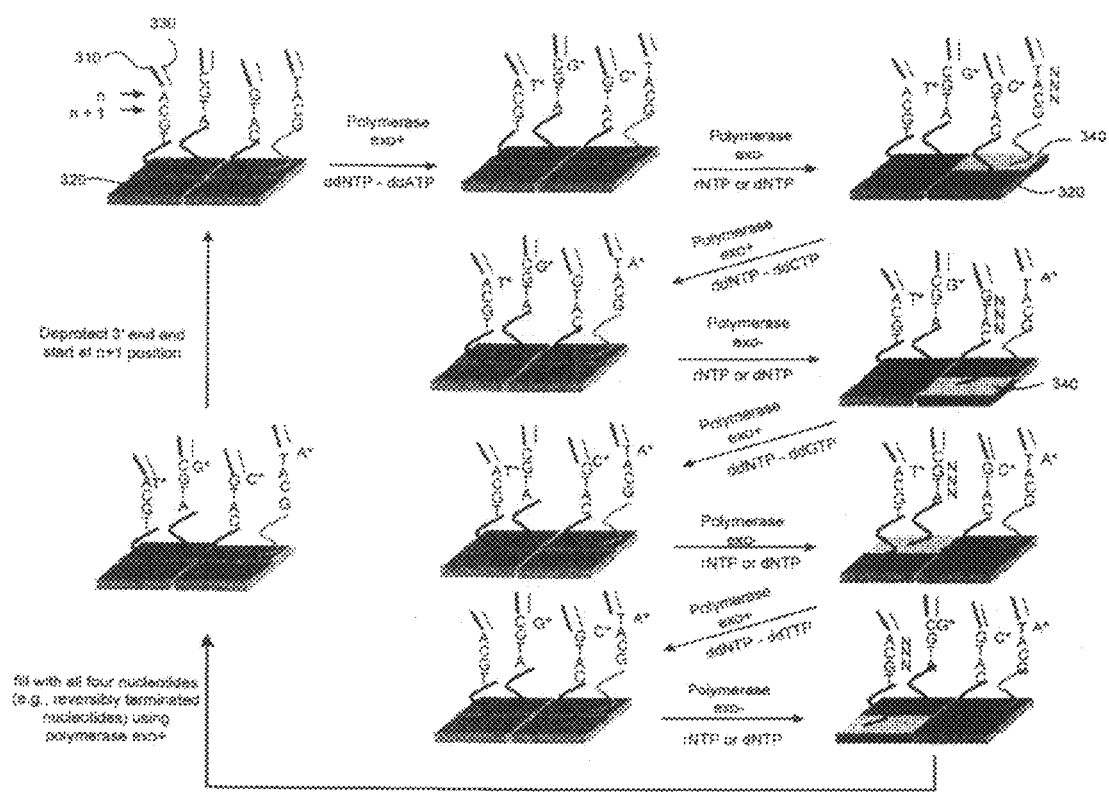
FIG. 3 shows an additional general scheme for sequencing nucleic acids using an array of sensors and alternating reversible determination.

FIG. 3 provides an additional exemplary method for sequencing nucleic acids using an array of sensors and the chemical amplification of sequencing signals based on alternating reversible termination and nucleic acid polymerization. In FIG. 3, nucleic acids to be sequenced 310 are immobilized on sensors 320, such that statistically there is one DNA molecule 310 immobilized on one sensor 320, and the DNA molecules to be sequenced 310 are primed with a complementary sequence of DNA 330 (a primer) that is terminated with a nuclease resistant nucleotide. Alternatively, a primer can be immobilized, and the DNA to be sequenced hybridized to the primer. A solution comprising a polymerase enzyme (polymerase exo+ which possesses exonuclease activity, such as for example, T4 and T7 DNA polymerases and Therminator II DNA polymerase) and a set of blocking nucleotides (such as, for example, dA*TP, dG*TP, dT*TP, and or dC*TP, the blocking function is indicated by a "*" in FIG. 3) that includes three of the four possible complementary nucleotides (e.g., dN*TP minus dA*TP) is supplied to the surface of the array of sensors 320 and the DNA primers 330 are then extended by a nucleotide that is complementary to the "$n^{th}$" base presented by the DNA to be sequenced 310. For DNA primers 330 that are hybridized to a nucleic acid to be sequenced 310 for which a complementary nucleotide has not been provided, no nucleotide is added to the primer 330. A solution comprising a polymerase enzyme ("polymerase exo–") or a DNA polymerase that is nondiscriminatory toward ribonucleotides (rNTPs, such as, for example, ATP, GTP, CTP, and UTP), nucleotides (such as, for example, dATP, dGTP, dUTP, dTTP, and dCTP or a mixture of dNTP and rNTPs) is supplied to the surface of the array of sensors 320 and the DNA primer 330 is then extended (and or extended and deconstructed) for primers 330 that are not terminated with a blocking nucleotide to generate an amplified signal in sensors 340. Performing the DNA synthesis reaction a plurality of times increases the concentration of the reaction products each time a nucleotide is added to the primer DNA molecule 330 and increases the amount of signal for detection. For example, adding five nucleotides to the primer strand provides a signal that is amplified five times over the signal that is created when only one nucleotide is added to the primer DNA molecule 330. A signal resulting from a change in reactants, such as an increase in the concentration of reaction products (e.g., nucleic acid polymer or released PPi and protons) is detected by sensors 340 but not by sensor(s) 320 where complementary blocking nucleotides were added in the previous reaction. Polymerization reactions are performed, for example, 10 to 1,000 times to amplify the signal obtained, depending on the sensor configuration and the need for amplification. In this example, the signals detected indicate that the next complementary nucleotide for an immobilized DNA to be sequenced 310 is adenosine. The sensor providing no signal indicates that a blocking complementary nucleotide was added to the primer DNA molecule 330 (assuming that a functional DNA is immobilized in the sensor). A nuclease activity from a separate enzyme or from a DNA polymerase is then used to remove the nucleotides that were added during signal detection. Exemplary nuclease enzymes include, Exonuclease T, Bal-31 nuclease, and RNase H. RNase H has activity toward digesting ribonucleotides in RNA:DNA complexes. In the same or in a separate reaction, the DNA synthesis blocking groups are then removed followed by removing the nucleotides using exonuclease activity. These reactions are repeated to identify all four bases for the "$n^{th}$" position for the DNA template molecule 310. After that, blocking nucleotides are removed and the $n^{th}$ position is filled by nuclease resistant 3' reversibly blocked nucleotides. The nucleotides are then deblocked and the DNA template molecules 310 are ready for sequencing the "$n+1^{th}$" position. A solution comprising a polymerase enzyme (polymerase exo+) and another set of blocking nucleotides (e.g., dN*TP minus dC*TP) is once again supplied to the surface of the array of sensors 320 and the DNA primer 330 is then extended by a blocking nucleotide that is complementary to the "n+1$^{th}$" base presented by the DNA to be sequenced 310. The primers 330, for which the DNA molecules to be sequenced 310 that were not complementary in the "n+1$^{th}$" position to the supplied blocking nucleotides, remain unblocked and available for further DNA elongation reactions. A solution comprising a polymerase enzyme ("polymerase exo–") and nucleotides (rNTP or dNTP) is supplied to the surface of the array of sensors 320 and the DNA primers 330 are then extended for primers 330 that are not terminated with a blocking nucleotides. The extension of the DNA primer 330 once again creates signal that is detected by the sensors 340 which indicates the identity of the next nucleic acid in the DNA to be sequenced 310. These reactions are repeated a plurality of times to assemble the sequences of the DNA 310 immobilized in the sensors 320.

Figure 4:
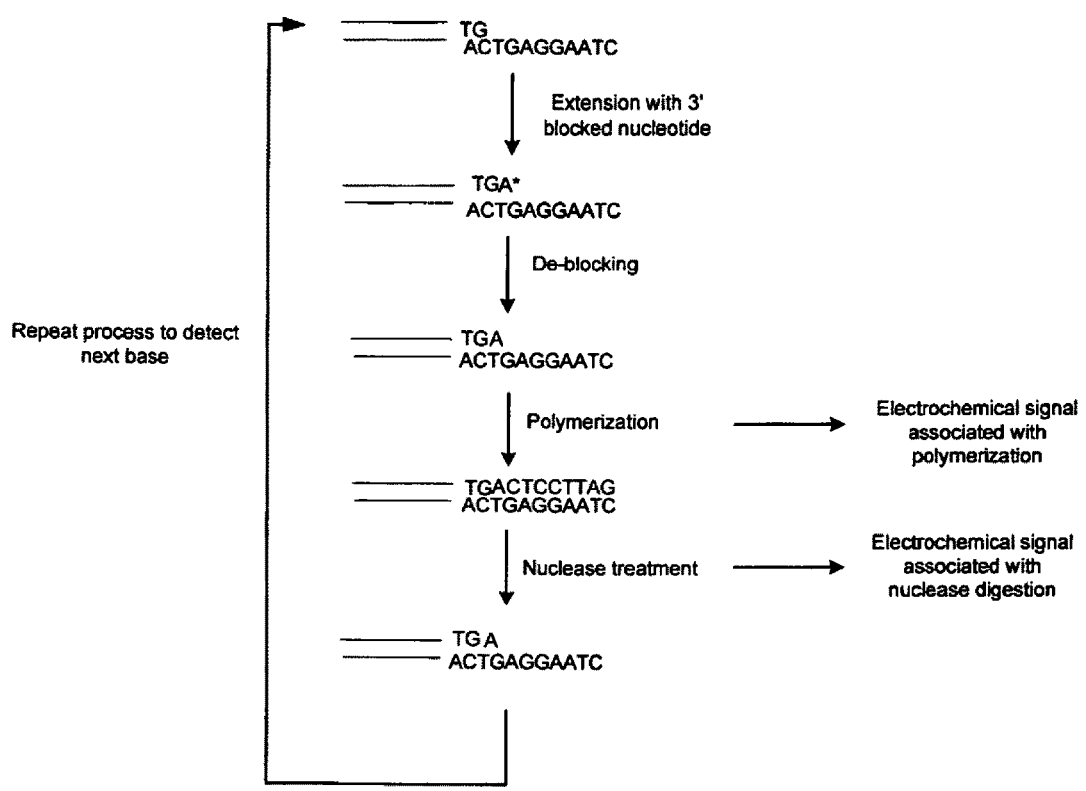
FIG. 4 demonstrates the production of an amplified chemical signal useful in DNA sequencing reactions.

FIG. 4 demonstrates in further detail how a detectable chemical signal is created in one instance in a sensor that is used to sequence a single molecule of a nucleic acid. In this example, a DNA fragment that is immobilized in a sensor has been primed with a complementary nucleic acid. A 3' blocked nucleotide (i.e., a nucleotide that is blocked from undergoing chain extension reactions through the action of a polymerase enzyme) that is complementary to the nucleic acid to be sequenced is added to the primer. The blocked nucleotide is unblocked and DNA extension is performed. Though the repeated monomer additions, reaction products build up and the sensor detects the reaction products from the polymer synthesis process. For example, the charge increase associated with the polymer chain extension can be detected electronically by the sensor. Optionally the synthesized nucleic acid can also be deconstructed through the action of an exonuclease enzyme and the reaction products of nucleic acid deconstruction can also be detected by the sensor. This process is repeated and the sequence is the DNA fragment is determined. FIG. 4 includes SEQ ID NO: 1 and SEQ ID NO: 2.

Figure 5:
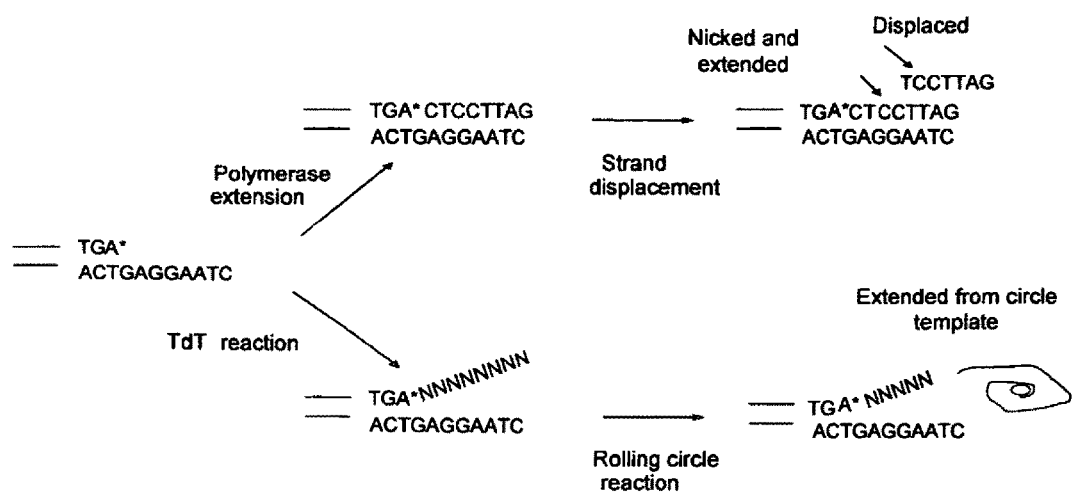
FIG. 5 provides examples of polymer extension reactions useful in DNA sequencing reactions.

FIG. 5 provides some exemplary nucleic acid extension reactions that are useful for generating amplified chemical signals. In FIG. 5, the "*" indicates a nuclease resistant bond between the first two previous nucleotides (in this example, between the G and the A). Chemical amplification of a sequencing signal can occur through a large number of base additions through, for example, nicking the synthesized polymer, displacing the newly synthesized nucleic acid polymer, and re-synthesizing a nucleic acid at the nick site. Enzymes such as Phi-29 DNA polymerase provide strong 3' exonuclease activity and strand displacement activity (commercially available from, for example, New England Biolabs, Inc., Beverly, Mass.). Alternatively, chemical amplification can occur through a large number of base additions resulting from a rolling circle synthesis process in which a nucleic acid is synthesized and extended from a circular nucleic acid template. The nucleotides used are, for example, naturally occurring dNTP, rNTP, or modified nucleotides. Any modified nucleotides that are compatible with enzymes for DNA synthesis and that can produce detectable changes in the reaction products (bound or released) of incorporation reactions can be used. (FIG. 7 provides examples of modified nucleotides.) The chemical amplification can additionally occur through TdT (terminal DNA transferase) tailing, in which deoxyribonucleotides, such as dTTP, are added repeatedly to the available primer nucleic acid strand. Enzymes such as terminal deoxynucleotide transferase provide template independent 3' terminal base addition for nucleic acid synthesis.

Figure 6:
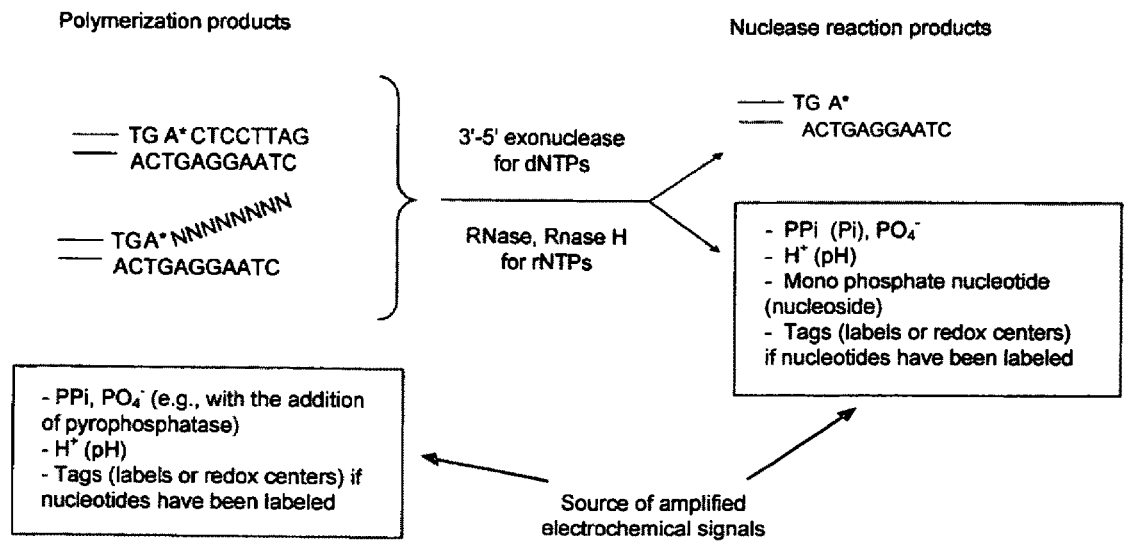
FIG. 6 shows exemplary chemical species that are amplified in nucleic acid sequencing reactions.

FIG. 6 shows some exemplary reaction products for nucleic acid synthesis that can be amplified and detected. In FIG. 6, "*" indicates nuclease resistant base. Reaction products from both the synthesis and deconstruction of nucleic acids can be detected. If a nucleoside triphosphate is incorporated into the growing strand in the test reaction, then a pyrophosphate (PPi) is released. The pyrophosphate can be degraded into two inorganic phosphates through ionic dissociation caused by water and catalyzed by pyrophosphatase. In an amplification reaction, an exonuclease is optionally used to remove the incorporated nucleoside monophosphates ($NMP^{-2}$), allowing another nucleoside triphosphate to be incorporated and a PPi to be released. The generation of pyrophosphate and/or phosphate can affect the local pH and the ionic strength of the reaction solution. Since each dNTP (or NTP) has four ionizable groups and its products have a total of eight ionizable groups, a net increase of four ionizable groups is realized through the incorporation-deletion reaction cycle. The incorporation-deletion reaction cycle can be repeated many times as long as a matched dNTP (or NTP) is present. For example, for ten rounds of incorporation-deletion cycles, assuming a reaction region having the dimensions of 100 nm in diameter and 100 nm in depth, the change in ionizable groups would be equal to 85 μm of monovalent ions. The increase in acidity and/or ionic strength can be sensed electronically, such as for example, with a reaction region coupled to a FET sensor (or electrodes). Repetition of these reactions provides linear amplification of inorganic phosphates. Optionally, the nucleotide that is incorporated into the growing polymer is labeled and a buildup of labels is detected. Additionally, when nucleotides (labeled or unlabeled) are polymerized, the total charge associated with the molecule to be sequenced (the template) increases and this increase can be detected electronically. The polymerized nucleotides can be removed after signal detection to regenerate the molecule for the next base determination.

The processes shown in FIGS. 2 and 3 can be integrated into a miniaturized device, such as a microfluidic or a nanofluidic device. Additionally, the methods shown in FIGS. 2 and 3 can be automated though the use of a computer to control the delivery of reagents and monitor the results from electrical or optical measurements, such as current flow in FETs, impedance between electrodes, or redox potentials of labels. Sequence data is assembled from multiple cycles of reactions. Further, the methods shown in FIGS. 2 and 3 can be performed in a highly parallel manner using an array of reaction regions (or wells) in which a nucleic acid to be sequenced is immobilized. Microscale fluidic devices typically have interior features for fluid flow and containment having diameters of 500 μm or less. A micrometer (μm) is $10^{-6}$ meters. Nanoscale fluidic devices typically have interior features for fluid flow and containment having diameters of 500 nm or less. A nanometer (nm) is $10^{-9}$ meters.

Figure 7A:
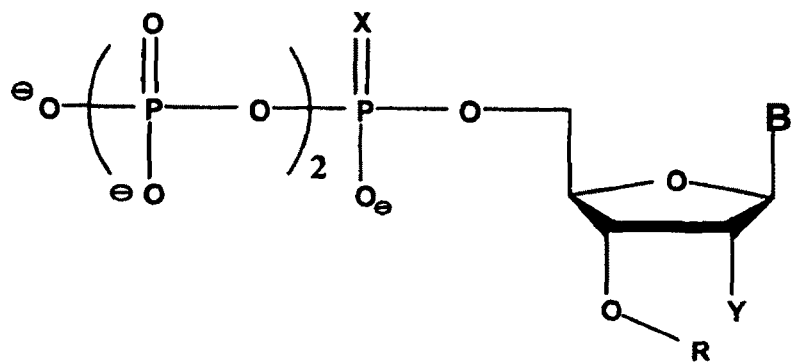
FIGS. 7A-7E show exemplary nucleotides that can be used for sequencing nucleic acids using methods employing the chemical amplification of signals related to nucleotide incorporation detection.

FIGS. 7A-7E provide examples of nucleotides and dinucleotides that are useful in sequencing nucleic acids according to embodiments of the invention. Additionally, the nucleotide can include more phosphate groups, it can be, for example, a tetra- or pentaphosphate. FIG. 7A shows exemplary nucleotides in which B is A, G, C, T, or analog thereof, R is a reversible terminator, Y is H or OH, and X is a sulfur or oxygen atom, a methyl group, or a —$BH_3$ group. When X is a sulfur atom, a methyl group, or a —$BH_3$ group, the nucleotide is a polymerase resistant nucleotide (an alpha-thiotriphosphate, alpha-methyltriphosphate, alpha-boranophosphate). The reversible terminator in FIG. 7A is, for example, an allyl, alpha-nitrobenzy group, or azidomethyl group.

Figure 7B:
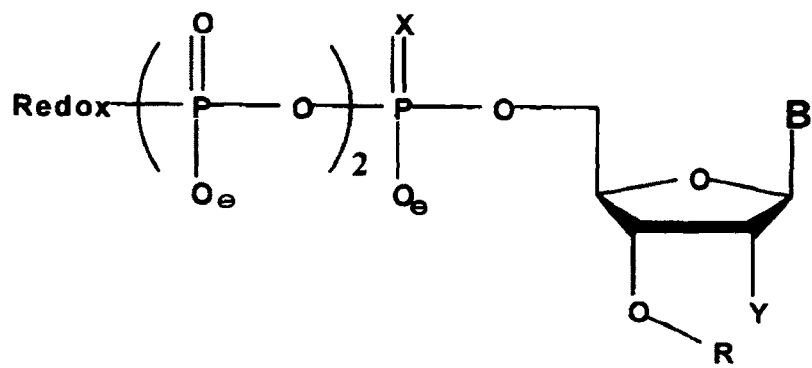

FIG. 7B shows exemplary releasable redox modified nucleotide triphosphates in which B is A, G, C, or T, R is a reversible terminator, Y is H or OH, and X is a sulfur or oxygen atom, a methyl group, or a —$BH_3$ group. When X is a sulfur atom, a methyl group, or a —$BH_3$ group, the nucleotide is a polymerase resistant nucleotide (an alpha-thiotriphosphate, alpha-methyltriphosphate, alpha-boranophosphate). The reversible terminator is, for example, an allyl, alpha-nitrobenzy group, or azidomethyl group. The redox center is, for example, a ferrocene, a 4-hydroxyphenol, a 4-aminophenol, or a napthyl. The incorporation of a complementary redox labeled nucleotide into the growing strand releases redox labeled pyrophosphate (PPi) group into solution. The action of a phosphatase enzyme removes the pyrophosphate from the redox molecule. Useful phosphatase enzymes include alkaline phosphatase, acid phosphatase, protein phosphatase, polyphosphate phosphatase, sugar-phosphatase, and pyrophosphatase. For example, the redox active species is the p-aminopheonol (pAP) and quinoneimine pair. The number of p-aminopheonol molecules released into solution is amplified through the repeated redox-modified nucleotide incorporations. Through these repeated cycles of incorporation, the concentration of the redox active species builds up in solution. In this way, the signal resulting from the incorporation of a complementary base into the growing complementary strand is amplified. The presence of the redox active species free of phosphate groups is detected electrochemically. Optionally, the redox active species are recycled between two electrodes to amplify the signal further. As described more fully herein, the signal amplification technique of cycling redox active species between electrodes is referred to as redox cycling. By moving between electrodes, each redox active species contributes multiple electrons to the measured current, thereby amplifying the measured current.

Figure 7C:
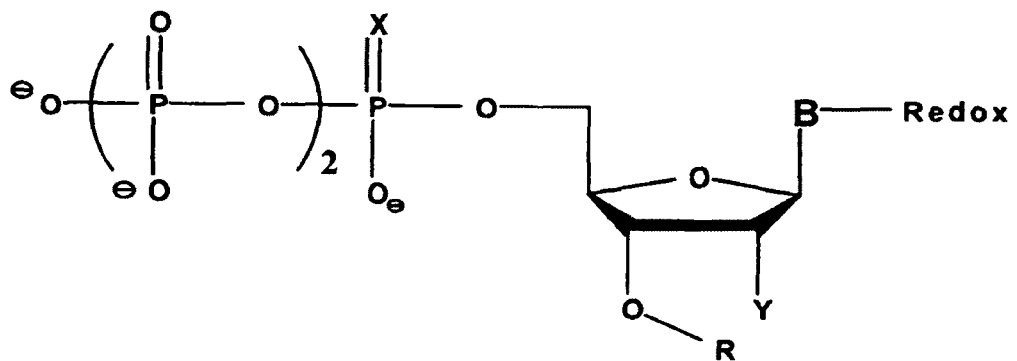
Figure 7D:
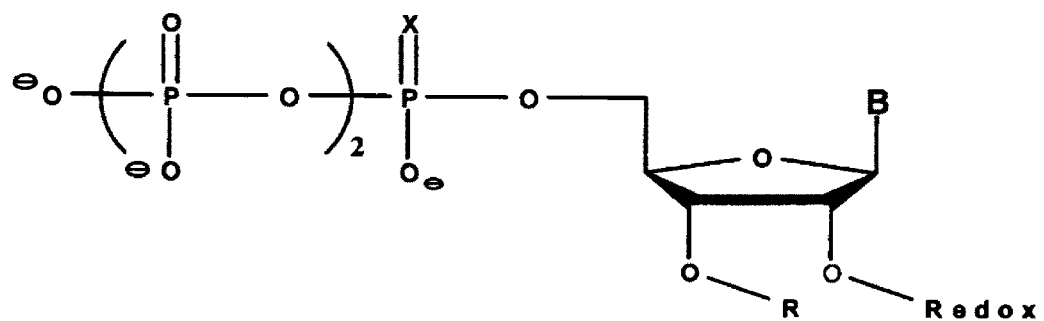

FIGS. 7C and 7D show exemplary non-releasable redox modified nucleotide triphosphates in which B is A, G, C, or T, R is a reversible terminator, Y is H or OH, and X is a sulfur or oxygen atom, a methyl group, or a —$BH_3$ group. When X is a sulfur atom, a methyl group, or a —$BH_3$ group, the nucleotide is a polymerase resistant nucleotide (an alpha-thiotriphosphate, alpha-methyltriphosphate, alpha-boranophosphate). The reversible terminator is, for example, an allyl, alpha-nitrobenzy group, or a azidomethyl group. The redox center is, for example, in FIG. 7C, ferrocene, methylene blue, anthraquininoe, 4-hydroxyphenol, or 4-aminophenol and in FIG. 7D, ferrocene, methylene blue, or antraquinone. The incorporation of a plurality of non-releasable redox modified nucleotide triphosphates into a nucleotide polymer provides an amplified signal from the plurality of attached redox centers. The presence of the redox centers is detected directly by sensor electrodes, or indirectly through mediator compounds or metal nanoparticles introduced to the reaction solutions (see, for example, *Anal. Chem.*, 78(8):2710-2716 (2006); *J. Am. Chem. Soc.*, 130(30):9812-9823 (2008); *Nature Biotechnology*, 21(10):1192-1199 (2003)). Nucleotides that have redox centers are removed after signal detection.

Figure 7E:
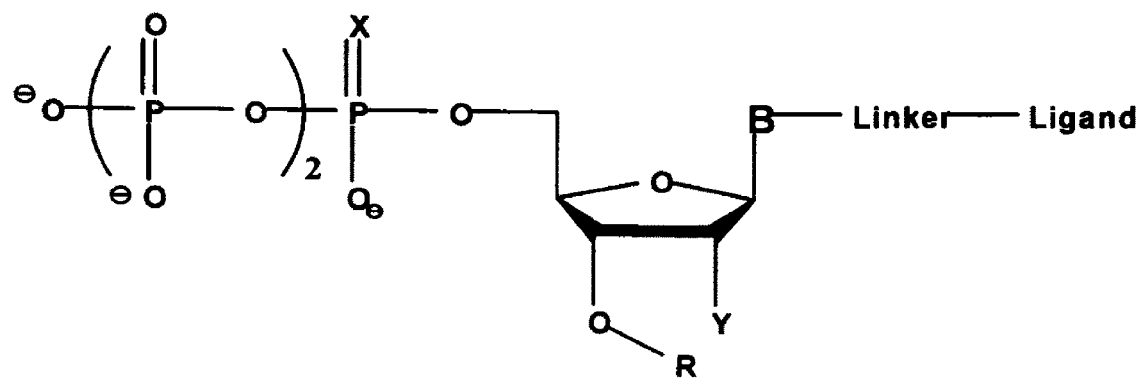

FIG. 7E shows exemplary ligand-modified nucleoside triphosphates in which B is A, G, C, or T, R is a reversible terminator, Y is H or OH, and X is a sulfur or oxygen atom, a methyl group, or a —$BH_3$ group. When X is a sulfur atom, a methyl group, or a —$BH_3$ group, the nucleotide is a polymerase resistant nucleotide (an alpha-thiotriphosphate, alpha-methyltriphosphate, alpha-boranophosphate). The linker is for example, a chemicleavable or photocleavable group, such as for example, azidomethyl group or allyl group, and the ligand is biotin or DIG (digoxigenin). DIG is considered to be a hapten, a small molecule with high immunogenicity. Other haptens include DNP (dinitrophenol), biotin, and fluorescein. In general, antibodies generated against haptens have higher affinities for their targets than antibodies toward different targets. When ligand-modified triphosphates are incorporated into a DNA molecule, affinity agents such as antibody-conjugated enzymes or antibody-conjugated nanoparticles can then be attached to the DNA molecule. Various methods can be used to detect the signal associated with the tag, such as, for example, detecting the products from enzyme mediated reactions (redox 4-aminophenol), detecting redox centers, or ionic species.

Typical useful polymerase enzymes include DNA polymerases with or without 3' to 5' exonuclease activities, such as for example, *E. coli* DNA polymerase I, Klenow fragment of *E. coli* DNA polymerase I, phusion DNA polymerase, Therminator DNA polymerase, reverse transcriptase, Taq DNA polymerase, Vent DNA polymerase (all available from New England Biolabs, Inc., Beverly, Mass.), T4 and T7 DNA polymerases, and Sequenase (all available from USB, Cleveland, Ohio). Nuclease-resistant nucleotides can be ribonucleotides or other modified nucleotides. A variety of polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant nucleotides that can be incorporated into growing DNA strands but that are resistant to digestion by exonucleases (such as the 3' to 5' exonuclease active DNA polymerases or exonuclease I and III) include alpha-phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases. Phi-29 DNA polymerase (available from New England Biolabs) provides strand displacement activity and terminal deoxynucleotide transferase provides template independent 3' terminal base addition.

Figure 8:
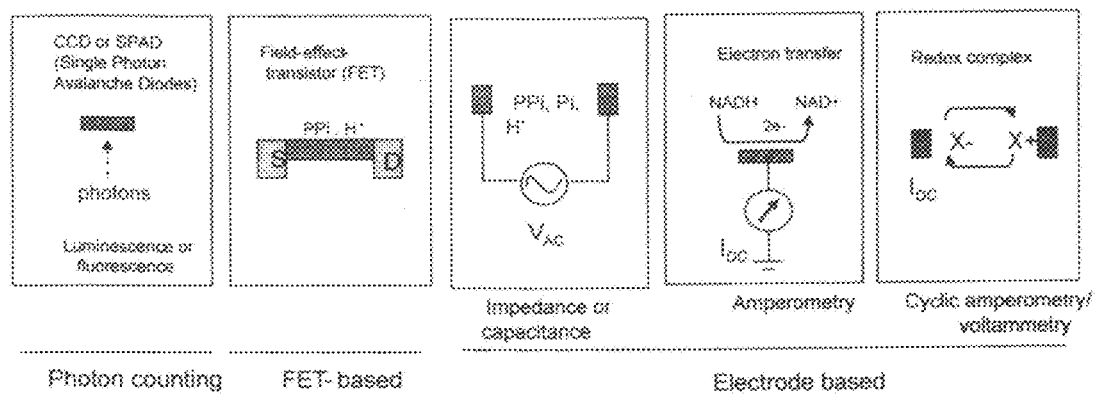
FIG. 8 shows exemplary sensing schemes that can be used to sequence nucleic acids using chemical amplification of signals.

FIG. 8 demonstrates exemplary detection schemes and devices useful for performing nucleic acid sequencing. Possible sensing schemes include ones that measure or otherwise provide a response based on the primary reaction product content, such as for example PPi, Pi, $H^+$, and polymerized nucleotides. In the alternative, sensing schemes can measure secondary products such as labels (modified nucleotides) and or the products of additional chemical reactions, such as for example, detecting the presence of photons, electron carriers, and or redox centers. Sensors include ones capable of photon counting, FET-based sensors, and electrode-based sensors that measure impedance or capacitance or that perform amperometry, cyclic amperometry, and or voltammerty. Discussions of the measurement of impedance or capacitance changes for biological molecules and reactions can be found, for example, in Daniels, J, Pourmand, N., *Electroanalysis*, 19:1239 (2007) and Daniels, J., Anderson, E., Lee, T., Pourmand, N., "Simultaneous Measurement of Nonlinearity and Electrochemical Impedance for Protein Sensing Using Two-tone Excitation," *Engineering in Medicine and Biology Society*, 30th *International Conference of the IEE* (2008). Micro and nanoelectrode arrays can be fabricated for electrode-based sensors. Electrodes can be fabricated as printed circuit boards. PPi is an important product of nucleotide incorporation by DNA polymerase and can be enzymatically converted to NADH in a set of cascade reactions (see, for example,

*Analytical Biochemistry,* 142(2):369-372 (1984)). NADH is an electron carrier that can donate 2 electrons upon oxidation.

Figure 9:
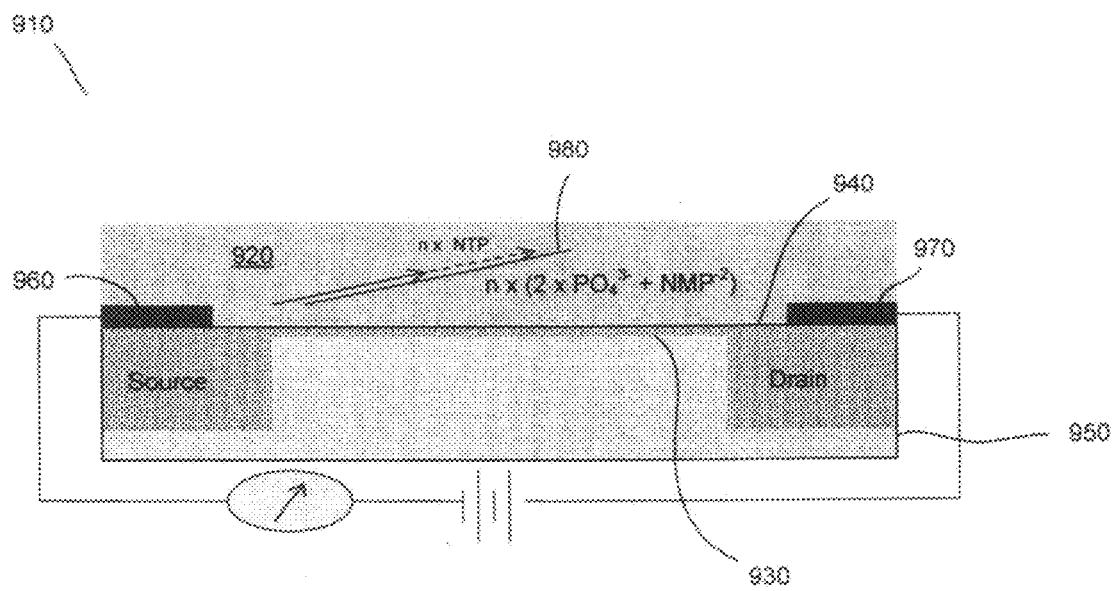
FIG. 9 is a schematic of device employing a field effect transistor that can be used for analyzing a solution-based nucleic acid sequencing reaction.

Referring now to FIG. 9, a sensor 910 for sensing a change in reactant or product concentrations resulting from DNA synthesis reactions. In the sensor 910 the amplified chemical signals from the polymerase reactions are converted into an electronic signal by an electronic sensor 910. For example, the sensor can be a P-type FET, an N-type FET, or a carbon nanotube transistor. See, for example, Janicki, M., Daniel, M., Szermer, M., Napieralski, A., *Microelectronics Journal,* 35, 831-840 (2004) and Rolka, D., Poghossian, A., Schoning, M., *Sensors,* 4, 84-94 (2004). In one embodiment, each sensor has a nano-sized reaction region 920 (the gate) and a semiconductor transistor (channel) 930 that are separated by an insulating layer 940. The insulating layer 940 can, for example, be made from silicon oxide, silicon nitride, aluminum nitride, and or silicon oxynitride. The channel 930 of the semiconductor transistor, for example, can be comprised of a P- or N-type semiconductor, as is well known in the art, such as for example, silicon or germanium doped with boron, arsenic, phosphorous, or antimony. A solution in the reaction region 920 forms a gate and the components of the sensor 910 are typically placed on a substrate 950. The source electrode 960 and the drain electrode 970 are typically comprised of conducting materials, as are well known in the art of chip fabrication, such as for example, gold, copper, silver, platinum, nickel, iron, tungsten, aluminum, or titanium. The substrate 950 can be comprised of, for example, silicon, silica, quartz, germanium, or polysilicon. In further embodiments, the reaction region 920 has dimensions of less than about 100 nm, less than about 1 µm, or less than about 10 µm. The reaction region can have dimensions in the range of 10 nm to 10 µm. The reaction region 920 is used as part of the gate of the transistor. DNA 980 can be immobilized in the region by standard methods. Acrydite-modified DNA fragments can be attached to a surface modified with thiol groups and amine-modified DNA fragments can be attached to epoxy or aldehyde modified surfaces. In operation, variations in the potential between the solution (the gate) in the reaction region 920 and the insulator 940 surface modify the charge distribution in the channel 930. Changes in the solution, such as changes in charge distribution created by the linearly amplified PPi molecules or bound charges associate with the DNA molecules, can be measured by changes in the conductivity or changes in the capacitance across the channel 930.

A further exemplary FET device, a double-gate silicon-on-silicon-insulator field effect device, that is optimized to maximize pH sensitivity, is discussed in Elibol, O., Reddy, B., Bashir, R., *Appl. Phys. Lett.,* 92:193904 (2008). (See also, Elibol, O., Reddy, B., Bashir, R., *Appl. Phys. Lett.,* 93:131908 (2008))

In additional embodiments, the sensor can comprise a carbon nanotube transistor. Carbon nanotube FET devices have been described. See, for example, Star, A., Gabriel, J.P., Bradley, K., Gruner, G., *Nano Letters,* 3:4, 459-463 (2003) and Fritz, J, Cooper, E.B., Gaudet, S., Sorger, P.K., Manalis, S.R., *Proceedings of the National Academy of Sciences,* 99:22, 4984-4989 (2002). In general, carbon nanotubes, such as for example, single-walled carbon nanotubes (SWNTs), that are useful in a FET device, can be made through the chemical vapor deposition of methane onto catalytic iron nanoparticles. Metal evaporation through a mask can be used to create the electrical contacts that form a source and a drain. DNA can be attached to the carbon nanotube transistor, for example, by coating the carbon nanotube with Tween-20™ (a non-ionic surfactant) or polyethylene oxide, which readily adsorb to the surface of the nanotube, activating the Tween-20™ (a non-ionic surfactant) or polyethylene oxide-containing polymer with a water-soluble carbodiimide coupling reagent, such as for example, 1,1-carbonyldiimidazole, for conjugation with coupling agents such as biotin, avidin, antigens, or antibodies. DNA molecules having a corresponding coupling agent can then be attached through the surface through, for example, a biotin-avidin or antibody-antigen interaction.

Figure 10:
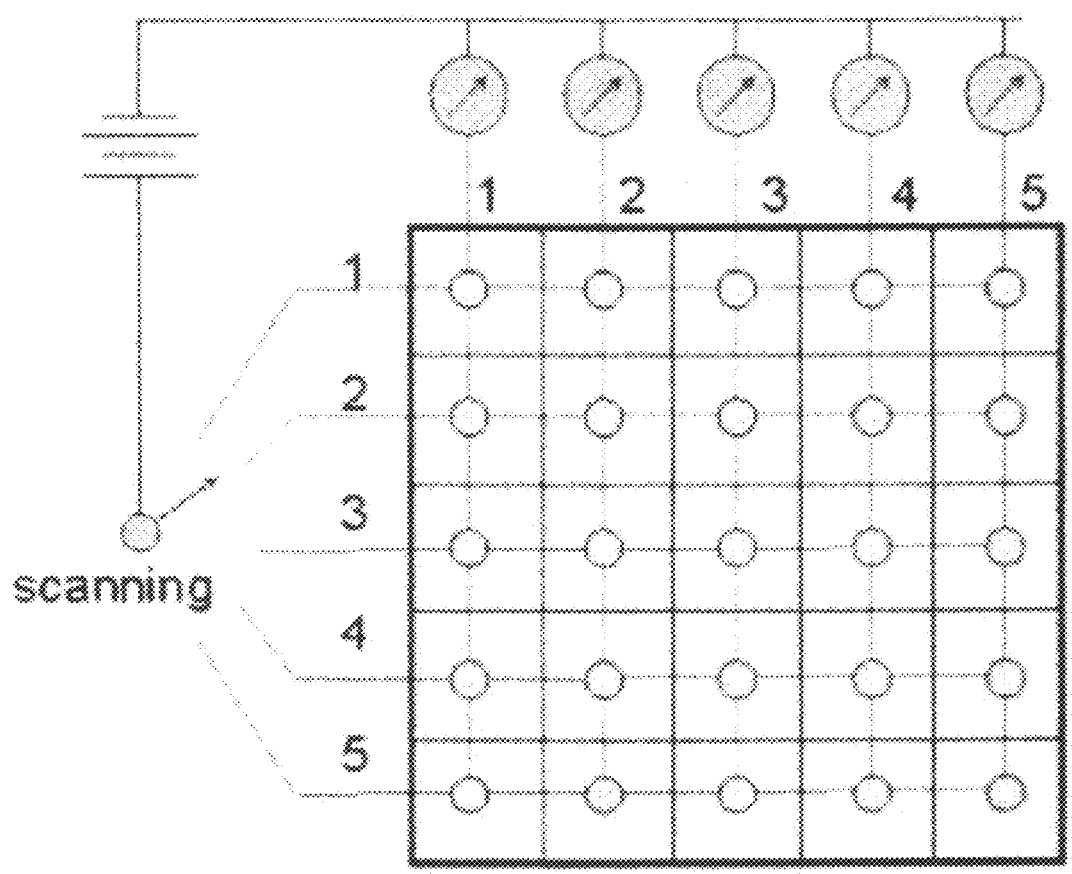
FIG. 10 is a schematic of an array of reaction sites employing field effect transistors that can be used for analyzing nucleic acid sequencing reactions.

Referring now to FIG. 10, an array of electronic sensors is shown. For simplicity, the array is shown having five rows and five columns of sensors, however the invention is not so limited and arrays can be built having a variety of dimensions and numbers of sensor regions. For example, arrays of sensors could be $10\times10$, $100\times10$, $1,000\times1,000$, $10^5\times10^5$, and $10^6\times10^6$. In FIG. 10, the sensors are depicted as FET sensors that are connected to a source line 1100 and a drain line 1110. A reaction region 1120 is shown in FIG. 10 having circular dimensions (a cavity), however embodiments of the present invention are not so limited and other shapes and dimensions are possible, such as for example, those having rectangular or other multisided configurations or even flat surfaces are possible. The reaction region 1120 forms part of the transistor gate. The FET sensors 1130 can be monitored individually or as a group. The sensor array allows many immobilized DNA molecules to be sequenced simultaneously. The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. Alternatively, a common adaptor sequence is ligated with the DNA molecule to be sequenced and the capture probe sequence is a universal sequence for all sequences to be sequenced. Typically, DNA fragments to be immobilized are diluted so that statistically each sensor has one DNA molecule immobilized. Information from FET sensors showing ambiguous results can be disregarded. Sequence information is assembled from the sensors having a single DNA molecule immobilized. Chemical information, such as for example a change in pH or in ionic concentration, from each reaction region is sensed independently. Micro and nano-structures on the array can be built to minimize diffusion. For example, wells can be built over each sensor, the sensor array can be placed upside down, well facing down, with the temperature in the down side lower than the chip side, and a low melting point gel (such as low melting point agarose) can be used to make the reaction mixture. Standard silicon and semiconductor processing methods allow a highly integrated sensor array to be made. For example, a $2.5\times5$ cm$^2$ silicon wafer chip can hold as many as $5\times10^9$ sensors that are about $0.5\times0.5$ µm$^2$ For example, it is calculated that only about 1 sensor array would be needed to sequence the whole human genome with $10\times$ coverage, assuming that 10% of the sensors on the array yield single molecule sequencing information and that each immobilized DNA molecule provides 60 bases worth of sequencing information.

In further embodiments of the present invention, chemical signal or bound charge amplification can be used in conjunction with optical detection in the sequencing reactions. Phosphate ions generated from amplification processes can be reacted, for example, with molybdate ions to form phosphomolybdate. The abundance of phosphomolybdate can be quantified optically by absorbance measurements at about 340 nm. Additionally, phosphomolybdate can be reduced and the resulting molybdenum blue optically detected at about 600 to about 840 nm. Useful reducing agents include, for example, aminonapthosulfonic acid, ascorbic acid, methylp-aminophenol sulfate, and ferrous sulfate. Alternatively, pyrophosphate molecules that are amplified from a test reaction can be converted to ATP by ATP sulfurase, and photons emitted by luciferase. See, for example, Ronaghi et al, *Science*, 281, 363-365 (1998). In another embodiment, phosphate and pyrophosphate ions form resorufin in presence of maltose, maltose phosphorylase, glucose oxidase, horse radish peroxidase, and Amplex Red reagent (10-acetyl-3,7-dihydroxyphenoxazine). The resorufin can be detected fluorometrically or spectrophotometrically. See, for example, *The Handbook—A Guide to Fluorescent Probes and Labeling Technologies* Molecular Probes, Section 10.3, available from Invitrogen.

Figure 11:
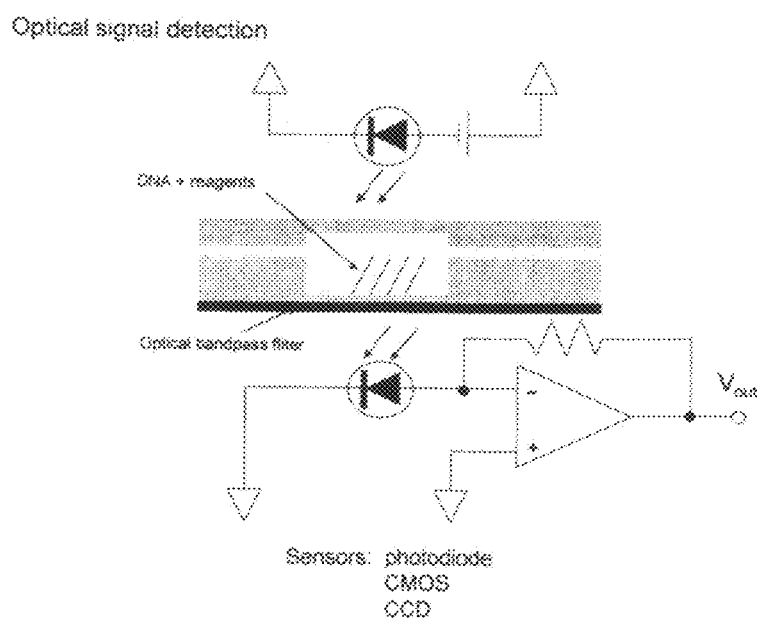
FIG. 11 shows a design for a microfluidic device that can be used for optically detecting the reaction products of a nucleic acid sequencing reaction.

FIG. 11 provides a schematic demonstrating a method by which signals from amplified reactions can be detected optically. Amplified chemical signals from the polymerase reactions are converted to an optical signal which is then converted into an electrical signal by an optical detector, for example, a photodiode, CMOS, or CCD detector. In one embodiment, each sensor has a nano-sized reaction region in the middle, a light emitting diode on one side, and a photodiode detector on the opposite side. Ideally the region is less than about 100 nm, however larger sizes are also useful, such as for example, regions that have dimensions that are less than about 10 μm in size. Optionally, a bandpass filter, which can be for example, a dielectric filter, can be placed between a photodiode/light emitting diode and the reaction region to tailor the wavelength of light transmitted. DNA can be immobilized in the reaction region by standard methods. The geometry of each reaction region (size, depth, shape and orientation) can be optimized to minimize reaction time. Optionally, the whole sensor can be packaged in an optically opaque material so that external light does not generate background noise.

Figure 12:
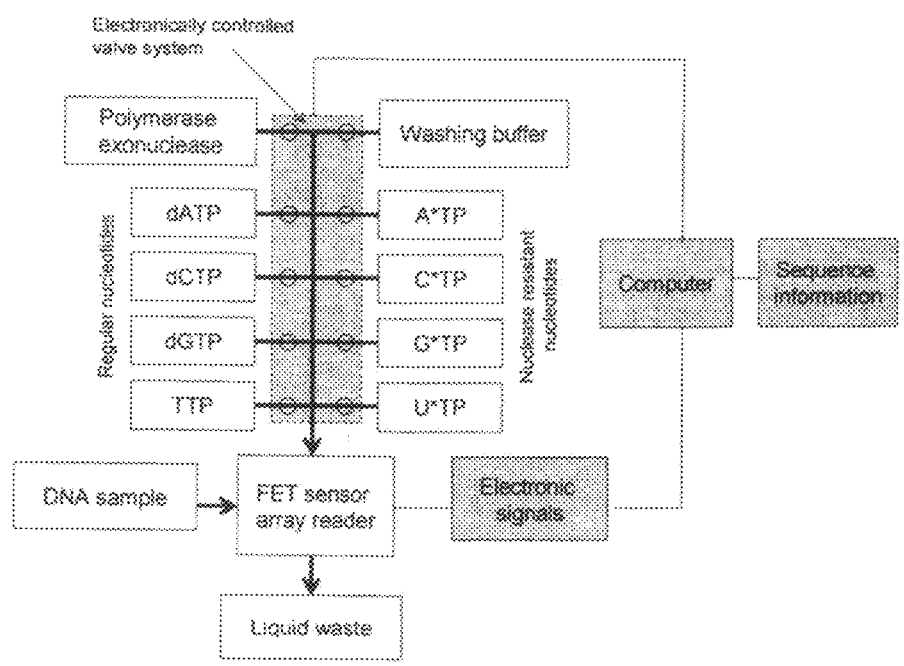
FIG. 12 shows a design for a system that can be used for sequencing nucleic acids.

In FIG. 12, a system that can be used for sequencing is shown. The system contains a fluidic system that regulates reagent delivery and waste removal, a computer that collects and analyzes sequence data, and an array reader that retrieves signals from the array. The array reader can be either an FET sensor array reader, an electrode based sensor array reader, or an optical sensor array reader. Reagent delivery and array washing can be controlled, for example with an electronic valve system. Fluid delivery can be controlled by a computer that sends signals to valve drives (not pictured) that control the electronic valve system.

Array compositions may include at least a surface with a plurality of discrete reaction regions. The size of the array will depend on the end use of the array. Arrays containing from about two to many millions of different discrete reaction regions can be made. Generally, the array size will depend in part on the size of the surface from which the array is made. Very high density, high density, moderate density, low density, or very low density arrays can be made. Some ranges for very high-density arrays are from about 1,000,000,000 to about 10,000,000,000 regions per array. High-density arrays range from about 1,000,000 to about 1,000,000,000 regions. Moderate density arrays range from about 10,000 to about 1,000,000 regions. Low-density arrays are generally less than 10,000 regions. Very low-density arrays are less than 1,000 regions.

The reaction regions can comprise a pattern or a regular design or configuration or can be randomly distributed. A regular pattern of regions can be used such that the regions can be addressed in an X-Y coordinate plane. The surfaces within the regions can be modified to allow attachment of analytes in individual regions. In general, reaction regions are a cavity, depression, or well in the surface of the substrate that is capable of containing a liquid. In alternate embodiments, no cavity, depression, or well is provided.

There are numerous suitable methods for patterning an array of nanoscale features on a surface of a substrate. Examples of such suitable methods include lithography methods such as, for example, interferometric lithography (IL), immersion interferometric lithography, electron beam lithography, scanning probe lithography, nanoimprint, extreme ultraviolet lithography, and X-ray lithography, and stamping, etching, microetching, and molding techniques. The technique used will depend in part on the composition and shape of the substrate. Generally, lithography is a highly specialized printing process used to create detailed patterns on a substrate, such as a silicon wafer. An image containing a desired pattern is projected onto the wafer, which is coated by a thin layer of photosensitive material called resist. The bright parts of the image pattern cause chemical reactions which, in turn, render the resist material soluble, and, thus, dissolve away in a developer liquid, whereas the dark portions of the image remain insoluble. After development, the resist forms a stenciled pattern across the wafer surface, which accurately matches the desired pattern. Finally, the pattern is permanently transferred into the wafer surface, for example by a chemical etchant, which etches those parts of the surface unprotected by the resist.

In various embodiments of the invention, arrays may be incorporated into a larger apparatus and/or system. In certain embodiments, the substrate may be incorporated into a microelectro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.*, 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

The electronic components of MEMS may be fabricated using integrated circuit (IC) processes (for example, CMOS, Bipolar, or BICMOS processes). The components may be patterned using photolithographic and etching methods known for computer chip manufacture. The micromechanical components may be fabricated using compatible micromachining processes that selectively etch away parts of the silicon wafer or add new structural layers to form the mechanical and/or electromechanical components.

Basic techniques in chip manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

In some embodiments of the invention, substrates may be connected to various fluid filled compartments, such as microfluidic channels, nanochannels, and or microchannels. These and other components of the apparatus may be formed as a single unit, for example in the form of a chip, such as semiconductor chips and or microcapillary or microfluidic chips. Alternatively, the substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

Techniques for batch fabrication of chips are well known in the fields of computer chip manufacture and or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. See for example, Craighead, *Science,* 290:1532-36, (2000). Various forms of microfabricated chips are commercially available from, for example, Caliper Technologies Inc. (Mountain View, Calif.) and ACLARA BioSciences Inc. (Mountain View, Calif.).

EXAMPLE 1

Sensor Array Fabrication: A field effective transistor array having $10^6$ sensors that are PPi sensitive is fabricated. The array is an Al—Si—$SiO_2$—$Ta_2O_5$ structure, fabricated from a p-Si wafer with specific receptivity of 1-10 Ohm/cm. A double layer that consists of 65 nm $SiO_2$ and 67 nm $Ta_2O_5$ which is made by thermal oxidation of sputtered Ta (Rolka, D., Poghossian, A., Schoning, M., *Sensors,* 4, 84-94 (2004)). Each sensor in the array is connected to an electronic circuit for signal amplification and data processing. Wells of 1×1×1 μm are constructed over each sensor using $SiO_2$ by standard photolithography techniques. The $SiO_2$ surface is modified to present free aldehyde groups through an aldehyde trimethoxysilane process (Lobert, P. E., Hagelsieb, L. M., Pampin, R., Bourgeois, D., Akheyar, A., Flandre, D., Remacle, J., *Sensors & Actuators B, Section μTas,* (2002)). Poly-T DNA oligo nucleotide is attached to the aldehyde surface as a universal capture probe. The 5' end of the DNA is modified with an amine group that can react with the aldehyde group through Shriff's reaction. The 3' end of the DNA is modified with alpha-thio-phosphodiester bond or a locked nucleotide so that capture probe is nuclease resistant. The array device is sandwiched between two peltier thermoelectrical coolers, which can be programmed and controlled by a computer.

Fluidic control: the sensor array surface is enclosed in a chamber made of plastic, with an inlet and outlet. The inlet is connected to reagent reservoirs and the outlet is connected to a waste chamber. Several reagent reservoirs are kept separate.

Reagents: major reagent solutions include: 1) Reaction buffer (also used as washing solution): 50 mM NaCl, 10 mM Tris-HCl (pH 7.9), 10 mM $MgCl_2$, 1 mM dithiothreitol, 100 μg/ml BSA; 2) Regular deoxyribonucleotides, dATP, dCTP, dGTP, dTTP, each kept separately at 100 μm in reaction buffer; 3) nuclease resistant blocking nucleotides (3' reversibly terminated alpha-phosphorothioate nucleotides), each kept separately at 50 μM in reaction buffer; 4) enzyme mix solution: T4 DNA polymerase at 0.1 unit/μl (with DNA polymerase activity and strong 3' to 5' exonuclease activity in the same enzyme) and pyrophosphotase at 0.001 unit/μl in reaction buffer; and 5) Therminator II DNA polymerase at 0.1 unit/μl.

DNA sample preparation: The sensor chip is a universal chip for DNA sequence detection, depending on DNA sample used. In this example, bacterial contamination in water is to be determined. A sample of water to be tested (1 L) is concentrated using a 0.22 μm filter. DNA is extracted from the sample with a DNA purification kit (Qiagen, Hilden, Germany), and digested to an average length of 200 bp by DNase I digestion, followed by exonuclease III digestion to yield single-stranded DNA. The 3' ends of the DNA fragments are modified by alpha-phosphorothioate dideoxyriboadenine triphosphate (ddATPαS) in a terminal transferase reaction, in which dATP and the dATPαS is in a 30:1 ratio. The modified DNA fragments will have a poly A tail, terminated with a nuclease resistant nucleotide.

DNA template immobilization: About 1 pg of the modified DNA fragments (about $1 \times 10^8$ copies) is added to the chip so that the DNA fragments are captured to the sensor wells through poly-A:poly-T hybridization. The density of the captured DNA molecules are controlled by hybridization time so that 1 fragment/senor on average. Alternatively, when the DNA molecules to be sequenced are tagged by fluorescent dye during the tailing reaction, the density of the DNA on sensor can be optically monitored. To stabilize the captured DNA on the sensor surface, photo-actable modified dATP can be used in the tailing reaction so that the captured DNA can be cross-linked with the modified poly-T capture probes ("Interstrand DNA cross-linking with dimers of the spirocyclopropyl alkylating moiety of CC-1065," *J. Am. Chem. Soc.,* 111: (16), 6428-6429(1989)).

Nuclease resistant blocking nucleotide incorporation and 3' reversible terminator cleavage: Therminator II DNA polymerase from New England Biolabs (NEB) is used at final 0.04 U/ul, 3'-azidomethyl dTTPαS is used at 200 μM in 1× Therminator II buffer (20 mM TrisHCl, pH8.8 10 mM KCl, 10 mM $NH_4SO_4$, 2 mM $MgSO_4$, 0.1% Triton X-100), 3'-azidomethyl group was removed with 50 mM TCEP (tris(2-carboxyethyl)phosphine) at pH 9. 65° C. and for 5 min.

Sequencing reaction: the reaction schemes described above and illustrated in FIG. 2 is used. The reaction procedure and steps, reagents and reaction conditions are as outlined in specification.

Data analysis: Recorded data from each sensor is analyzed. Sensors with no information or unidentifiable information from each step are ignored for further data analysis. The rest of the data is analyzed as follows: the frequency of given sequences is calculated, the sequence information is analyzed based on sequence alignment based on fragments of similar frequency to generate longer fragment information, and the assembled sequence is searched against a database of know sequences.

EXAMPLE 2

Terminal DNA Transferase (TdT) Tailing

DNA immobilization procedure: A gold surface chip was cleaned with hexane, methanol, and water, and dried with nitrogen gas. A solution of 1 μM HS-ssDNA in 1.0 M $NaH_2PO_4$ (pH=3.8) was prepared. To a pre-cleaned glass vial (20 mL), 2 ml of prior solution was added, and the chip (with the gold electrodes facing up) was immersed over night (17 hrs). The chip was dipped into 100 mL DI water for several seconds and the HS-ssDNA-treated surface was placed in a solution of 1.0 mM MCH (mercaptohexanol) dissolved in pure water for 1 hr. The chip was rinsed and stored in DI water at 4° C. until testing.

Typical TdT reaction: TdT enzyme was purchased from new England Biolabs (MA, USA) and reactions took place in 50 ul solution containing 20 units of TdT, 20 mM Tris-acetate, 50 mM K-Acetate, 10 mM MgCl$_2$, and 1 mM DTT (dithiolthreitol), at pH 7.9, 200 uM dATP, 2.5 mM CoCl$_2$. The reaction was incubated at 37° C. for 30 min.

Method for impedance measurement: 1) Parallel impedance measurements were made for both control (no TdT tailing) and experiment (TdT tailing); 2) In addition to selected sinusoidal frequencies, an extended range of frequencies (0-500 Hz) of 500 mVp-p voltage were applied in pseudo-random sequences to further explore impedance profiles.

Result: the admittance (1/impedance) increased significantly after tailing reaction and removal of excess salts from the gold electrode device.

The invention claimed is:

1. A method for determining sequences of a sample of DNAs to be sequenced comprising, providing an array comprising a plurality of regions, and a sensor;

hybridizing primer strands of DNA to the DNAs to be sequenced wherein the hybridized primer strands of DNA are terminated with a nuclease-resistant nucleotide, and wherein statistically one DNA to be sequenced is immobilized in one region;

providing a first set of reactants to the regions, the first set of reactants comprising nuclease-resistant blocking nucleotides comprising only one type of base among adenine, guanine, thymine and cytosine, and being capable of preventing extension of a DNA molecule and capable of preventing cleavage of the nuclease-resistant blocking nucleotides from a DNA molecule by a nuclease, after the nuclease-resistant blocking nucleotides are incorporated into the DNA molecule, and an enzyme capable of extending a DNA molecule;

incorporating the nuclease-resistant blocking nucleotides into primer strands hybridized to those DNAs to be sequenced whose next unpaired base is complementary to the only one type of base comprised by the nuclease-resistant blocking nucleotides;

providing a second set of reactants to the regions, the second set of reactants comprising nucleotides selected from a group consisting of analogs of nucleotides, adenine, guanine, thymine and cytosine; and an enzyme capable of extending a DNA molecule;

extending hybridized primer strands to which the nuclease-resistant blocking nucleotides are not incorporated, with the nucleotides and/or the analogs of nucleotides;

detecting with the sensor increases in reaction products in the regions resulting from the extending hybridized primer strands with the nucleotides and/or the analogs of nucleotides;

removing the nucleotides and/or the analogs of nucleotides that extended the hybridized primer strands, from the hybridized primer strands; and determining sequence information for the sample of DNAs to be sequenced based on detected increases in reaction products by the sensor.

2. The method of claim 1 wherein the array comprises about 2 to about 10,000 regions.

3. The method of claim 1 wherein the array comprises about 10,000 to about 1,000,000,000 regions.

4. The method of claim 1 wherein the sensor is a field effect transistor.

5. The method of claim 1 wherein the sensor is comprised of single walled carbon nanotubes that are capable of acting as a field effect transistor.

6. The method of claim 3 or 4 wherein detecting increases in reaction products comprises detecting a change in current flow in a field effect transistor.

7. The method of claim 1 wherein the sensor is an electrode.

8. The method of claim 1 wherein the enzyme capable of extending a DNA molecule is a polymerase enzyme.

9. A method for determining sequences of a sample of DNAs to be sequenced comprising, providing an array comprising a plurality of regions, and a sensor;

hybridizing primer strands of DNA to the DNAs to be sequenced wherein the hybridized primer strands of DNA are terminated with a nuclease-resistant nucleotide, and wherein statistically one DNA to be sequenced is immobilized in one region;

providing a first set of reactants to the regions, the first set of reactants comprising blocking nucleotides comprising only three types of bases among adenine, guanine, thymine and cytosine, and being capable of preventing extension of a DNA molecule, after the blocking nucleotides are incorporated into the DNA molecule, and an enzyme capable of extending a DNA molecule;

incorporating the blocking nucleotides into primer strands hybridized to those DNAs to be sequenced whose next unpaired base is complementary to one of the only three types of bases comprised by the blocking nucleotides;

providing a second set of reactants to the regions, the second set of reactants comprising nucleotides selected from a group consisting of analogs of nucleotides, adenine, guanine, thymine and cytosine; and an enzyme capable of extending a DNA molecule;

extending hybridized primer strands to which the blocking nucleotides are not incorporated, with the nucleotides and/or the analogs of nucleotides;

detecting with the sensor increases in reaction products in the regions resulting from the extending hybridized primer strands with the nucleotides and/or the analogs of nucleotides;

removing the nucleotides and/or the analogs of nucleotides that extended the hybridized primer strands, from the hybridized primer strands;

removing the blocking nucleotides, from the hybridized primer strands;

incorporating a nuclease-resistant blocking nucleotide to the hybridized primer strands;

determining sequence information for the sample of DNAs to be sequenced based on detected increases in reaction products by the sensor.

10. The method of claim 9 wherein the array comprises about 2 to about 10,000 regions.

11. The method of claim 9 wherein the array comprises about 10,000 to about 1,000,000,000 regions.

12. The method of claim 9 wherein the sensor is a field effect transistor.

13. The method of claim 9 wherein the sensor is comprised of single walled carbon nanotubes that are capable of acting as a field effect transistor.

14. The method of claim 12 or 13 wherein detecting increases in reaction products comprises detecting a change in current flow in a field effect transistor.

15. The method of claim 9 wherein the sensor is an electrode.

16. The method of claim 9 wherein the enzyme capable of extending a DNA molecule is a polymerase enzyme.

* * * * *

SEQUENCE LISTING

```
<160> NUMBER OF SEQ ID NOS: 2

<210> SEQ ID NO 1
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 1
actgaggaat c                                                        11

<210> SEQ ID NO 2
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 2
gattcctcag t                                                        11
```